United States Patent
Fernando et al.

(10) Patent No.: US 10,501,472 B2
(45) Date of Patent: Dec. 10, 2019

(54) **METHOD TO ISOLATE INOSCAVIN A FROM *FULVIFORMES FASTUOSUS* AND MEDICINAL PREPARATION THEREOF TO TREAT RHABDOMYOSARCOMA CANCER CONDITIONS**

(71) Applicants: University of Colombo, Colombo (LK); National Research Council, Colombo (LK)

(72) Inventors: Dilusha Fernando, Bandaragama (LK); Ravi Wijesundera, Maharagama (LK); Preethi Soysa, Colombo (LK); Dilip de Silva, Moratuwa (LK); Chandrika Nanayakkara, Pannipitiya (LK); Achyut Adhikari, Kathmandu (NP)

(*) Notice: Subject to any disclaimer, the term of this patent is extended or adjusted under 35 U.S.C. 154(b) by 90 days.

(21) Appl. No.: 15/775,007

(22) PCT Filed: Nov. 23, 2015

(86) PCT No.: PCT/IB2015/059027
§ 371 (c)(1),
(2) Date: May 10, 2018

(87) PCT Pub. No.: WO2017/013477
PCT Pub. Date: Jan. 26, 2017

(65) Prior Publication Data
US 2018/0370985 A1 Dec. 27, 2018

(30) Foreign Application Priority Data
Jul. 22, 2015 (LK) .............................. LK/P/1/18323

(51) Int. Cl.
*C07D 493/20* (2006.01)
*A61K 31/366* (2006.01)
*A61K 36/07* (2006.01)

(52) U.S. Cl.
CPC .......... *C07D 493/20* (2013.01); *A61K 31/366* (2013.01); *A61K 36/07* (2013.01)

(58) Field of Classification Search
CPC ................................................... C07D 493/20
See application file for complete search history.

(56) References Cited

PUBLICATIONS

"MeSH Browser", https://meshb.nlm.nih.gov/record/ui?ui=D012208, accessed Jun. 28, 2019 (Year: 2019).*
Kim. Tetrahedron Letters, 1999, 40, 6643-44. (Year: 1999).*
Lee. Journal of Natural Products, 2006, 69(2), 299-301 (Year: 2006).*
Lee. Natural Product Communications, 2010, 5(12), 1927-30 (Year: 2010).*

* cited by examiner

*Primary Examiner* — Noble E Jarrell

(57) ABSTRACT

The invention relates to a novel method to isolate a natural product, a flavonoid namely inoscavin A from a Sri Lankan mushroom, medicinal preparation thereof to treat rhabdomyosarcoma cancer condition. This compound was isolated from the terrestrial basidiomycete *Fulviformes fastuosus* for the first time. The isolation method of the inoscavin A comprises the following steps of: (1) carrying out sonication extraction of pulverized specimen by methanol; (2) partitioning in to hexane, dichloromethane and ethyl acetate respectively by liquid-liquid extraction 3) fractionation using normal phase silica gel column chromatography 4) purification using preparative high performance liquid chromatography (HPLC) to obtain flavonoid compound inoscavin A in substantially purified form (≥98%). In vitro cytotoxicity experiments demonstrated that the composition comprising inoscavin A strongly induced the apoptosis of human rhabdomyosarcoma (RD) cells compared to the cytotoxicity produced on normal epithelial cells (CC-1). Therefore, isolated flavonoid compound can be used for manufacturing of a medicament to treat rhabdomyosarcoma cancer condition. A method of treating rhabdomyosarcoma using medicinal preparation comprising inoscavin A can be achieved by administering said composition to a subject in need of such treatment.

5 Claims, 1 Drawing Sheet

METHOD TO ISOLATE INOSCAVIN A FROM *FULVIFORMES FASTUOSUS* AND MEDICINAL PREPARATION THEREOF TO TREAT RHABDOMYOSARCOMA CANCER CONDITIONS

FIELD OF THE INVENTION

The present invention discloses a novel method to isolate a natural flavonoid; inoscavin A indicated in formula 1, from mushroom *F. fastuosus*, having promising antiprolifertive activity on rhabdomyosarcoma and thereby communicates its application to use it as a medicinal provision for rhabdomyosarcoma.

ABBREVIATIONS $IC_{50}$: 50% inhibitory concentration; $CC_{50}$: 50% cytotoxic concentration; PBS: phosphate-buffered saline; DMSO: dimethyl sulfoxide; MTT: 3 4, 5-(dimethylthiazol-2-yl) 2-5-diphenyl tetrazolium bromide, SI: selectivity Index, HPLC: High Performance Liquid Chromatography, $^1$H-NMR: proton NMR, DEPT$^{13}$C-NMR: Distortionless Enhancement Polarization Transfer $^{13}$C NMR, COSY: H-H Correlation Spectroscopy, HSQC: Heteronuclear Single Quantum Correlation, HMBC: Heteronuclear Multiple Bond Correlation, NOESY: Nuclear Overhauser Effect Spectroscopy, HRE-IMS: High Resolution Electrospray Ionization Mass Spectrometry.

BACKGROUND OF THE INVENTION

Mushrooms have been valued by humankind as a source of nutrition, medication and numerous other purposes in the far eastern and recently in the western world. Mushrooms are an immensely rich source of biologically active secondary metabolites. Secondary metabolites are generated as a response to external stimuli such as nutritional or climatic changes. Usually, they are accumulated in only certain parts of the mushroom. The secondary metabolites produced by mushrooms exhibit largely diverse structural differences. Therefore, the isolation and separation process can be lengthy and tedious. However, isolation of natural products usually combines various separation techniques, which depend on the solubility, volatility and stability of the desired compound to be separated. Hence, the choice of different separation steps is of greater significance and an analytical-scale optimization of the separation parameters is worthwhile to make the isolation process shorter and convenient.

The first step in the process of obtaining secondary metabolites from biogenic materials is to extract them from the cellular matrix by means of extraction. The choice of extraction method is of greater importance due to the complex composition of the material and the minute amounts of the constituents available. An incorrect choice will cause the entire isolation process failed. In such cases, some or all of the targeted components of the specimen cannot be released satisfactorily from the matrix. Thereby, it is essential to select a suitable extraction method to obtain the total extract which is referred to as the crude extract. A logical next step in the isolation is to separate the desired components from the crude extract. This can be accomplished by liquid-liquid partition or by some low-resolution chromatographic isolation including normal phase column chromatography and size-exclusion chromatography. The goal of these steps is to concentrate the components of interest in order to facilitate the final purification steps. The third phase in the isolation usually involves high-resolution method to separate the desired compounds from the other components which remain in the extract. Since undesired components of the extract are likely to bear some closeness to the targeted compounds, requisite for optimization of the separation method become an important concern to accomplish sufficient resolution in the final preparative isolation. Frequently, the final isolation step involves liquid chromatography, preferably, high-pressure liquid chromatography (HPLC), counter-current chromatography (CCC), droplet counter-current chromatography (DCCC), rotation locular counter-current chromatography (RLCC), centrifugal partition chromatography (CPC).

In current invention, a novel and easy isolation method has been optimized to isolate inoscavin A compound of formula 1 from the Sri Lankan mushroom *Fulviformes fastuosus* to get rid and overcome above difficulties encountered during a separation and isolation process. Being a tropical country, Sri Lankan biota has enormous fungal diversity and consists of a variety of macrofungi species with medicinal and aromatic values. Although, some of the species are used in traditional medicine, most of them have been still not discovered for their medicinal values. Therefore, it is worthwhile to investigate the bioactive properties of unexplored mushrooms in order to discover medicinally important compounds of natural origin. Hence, this study is focused on antiproliferative activity of an unexplored macrofungus, *Fulviformes fastuosus* which is harvested from the dry zone forest reserves in Sri Lanka. Yet there are no reports available on bioactive properties of this species. *F. fastuosus* is a terrestrial basidiomycete which belongs to the family hymenochaetaceae. Majority of the species in this family are of medicinal value, while some are plant pathogens causing a white rot.

The last decade has witnessed the overwhelming interest of western research fraternity in pharmaceutical potential of mushrooms. Constituent molecules of mushrooms organelles and secondary metabolites have long been believed to possess pharmacologically important properties including antioxidant, anticancer, immunomodulatory, anti-inflammatory and anti-diabetic properties. There are approximately 650 species of macro fungi that have been reported to possess anticancer activity. The anticancer activity of the macrofungi was first reported for the extracts of fruiting bodies of *Boletus edulis* against the sarcoma 180 line in mice. The mounting evidences from various scientific studies across the world, regarding antitumor application of mushroom extracts and substances unarguably make it a fast-track research area worth mass attention. In spite of the availability of novel antineoplastic agents, cancer remains as the second leading cause of death affecting millions of people per year. The recent cancer therapies such as radiotherapy, chemotherapy and hormonal therapy have been made a modest progress in reducing the morbidity and mortality caused by cancer to the expected level and also produce unpleasant side effects. Hence, there is a recent upsurge in the interest of natural sources including mushrooms due to their promising anticancer properties. Molecules derived from medicinal mushrooms play a dominant role in the discovery and development of effective drug leads for cancer. The antitumor compound calvacin was the most commonly used natural product isolated from a mushroom. It was isolated from the giant puffball *Calvatia gigantean* and found activity against many experimental tumors, including mammary adenocarcinoma 755, sarcoma 180, leukemia L-1210, and HeLa cell lines. Moreover, Lentinan, schizophyllan and krestin are the natural products isolated from *Lentinus edodes*, *Schizophyllum commune*, *Trametes versicolor* mushrooms respectively. Currently, they have been approved in Japan as prescription drugs for the treatment of cancer. *Ganoderma lucidum* is also an important medicinal mushroom used today, acclaimed as "mushroom of immortality". Polysaccharide (GLPS) fractions isolated from *G. lucidum* have been reported to possess strong antitumor effect.

Inoscavin A flavonoid isolated from *Phellinus* species via a different isolation method have demonstrated in vitro inhibition of cell proliferation against HepG2, MGC80-3, HCT-116, HeLa, MCF-7 and A549 cancer cell lines. In current invention, inoscavin A has been isolated from an unexplored mushroom, *Fulviformes fastuosus* using a novel and convenient method and composition comprising inoscavin A thereof to treat rhabdomyosarcoma cancer conditions. In vitro cytotoxicity of the inoscavin A has been tested against rhabdomyosarcoma (RMS) using RD cell line. RMS is the most common soft tissue malignancy in childhood and soft tissue sarcomas (STS) constitute about 7% of all malignancies in children and adolescents under the age of 20 years. RMS is characterized by a high grade of malignancy, local invasiveness and a marked tendency to metastasize, while generating good response to chemotherapy and radiotherapy. RMS accounts for about 40% of pediatric soft tissue malignancies. Approximately 65% of cases diagnosed in United States have been identified as RMS in children less than six years old and approximately 250 new cases are detected each year in the USA. The incidence of RMS in Iraq is about 3% of childhood cancer cases less than 14 years of age in 2010. RMS is arisen from skeletal muscle precursors and divides in to two major subtypes, embryonal and alveolar, which differ prominently in their outcomes. Embryonal RMS usually occurs in children less than 10 years old with 5 year survival rate which is closer to 75%. Alveolar RMS presents throughout childhood and adolescence and is accompanying with poor prognosis with a 5 year survival rate below 50%. Prognosis of the patients with obstinate or relapsed RMS is worse, displaying lower survival rates ranging from 10 to 30%.

Different RMS cell lines can be used in basic research and preclinical testing for RMS. RD cells are one of the most commonly used cell line in RMS research. Therefore, RD cell line is used in the current study to determine the anticancer effect of inoscavin A. RD cell line is derived from a biopsy of 7 year old child having pelvic refractory RMS, previously treated with cyclophosphamide and radiation. It has been found that RD exhibited growth inhibition to cyclophosphamide and vincristine. Tolfenamic acid was also tested against RD cell line and showed decreased tumor size and reduction of cell migration after treatment. However, limited number of agents including natural sources has been tested yet against RMS. Current invention is ultimately targeted the investigation of anticancer activity of isolated compound inoscavin A against RMS and found that it is capable to induce apoptosis of RD cells. In addition, antiproliferative activity of inoscavin A against normal mammalian cell line (CC-1) was also investigated to compare the toxicity produced by inoscavin A against cancerous and normal cells by determining the selectivity index (SI). Selectivity index or therapeutic index is defined as the relative effectiveness of the investigational product in inhibiting tumor cell growth compared to inducing cell growth of normal cells. It is evaluated by the ratio of $CC_{50}/IC_{50}$. Inoscavin A, tested against RD cells exhibited an extremely large value for therapeutic index giving maximum antiproliferative activity for cancer cells with minimal toxicity for normal cells. Thereby, inoscavin A isolated from above described method can be effectively developed as a medicament for RMS. To the best of our knowledge, this is the preliminary and novel record that a natural product isolated from a mushroom being tested against rhabdomyosarcoma possesses potent anticancer effect.

SUMMARY OF THE INVENTION

The invention describes a novel method to isolate a natural flavonoid from *F. fastuosus* to use as a medicinal provision for rhabdomyosarcoma. Extraction method was begun with the carrying out sonication extraction of pulverized material of the fruiting bodies by methanol. Dried methanol extract was dissolved in water, and partitioned in to hexane, dichloromethane and ethyl acetate respectively by liquid-liquid extraction. The ethyl acetate layer was dispensed and dried in a rotary evaporator to obtain the dried extract. Dried ethyl acetate extract was subjected to normal phase silica gel column chromatography to afford a series of fractions that are enriched with the present compound. Preferred fractions with the desired compound were dried and preferably washed with acetone, to afford the compound by removing the impurities. The purified product inoscavin A; a yellow colour compound can be obtained in substantially purified form (≥98%) using reverse phase preparative high performance liquid chromatography (HPLC).

Anticancer activity of the isolated product against rhabdomyosarcoma for RD cell line and normal mammalian cell line; mice epithelial cells (CC-1) were determined in vitro. The cytotoxic effect of inoscavin A was further studied by evaluation of the selectivity index after estimating 50% inhibitory concentration ($IC_{50}$) for RD cell line and 50% cytotoxic concentration ($CC_{50}$) value for CC-1 cell line. Astoundingly, inoscavin A from *F. fastuosus* exhibits a remarkably lower $IC_{50}$ value (12.8 ng/ml or 27.99 nM) against RD cell line showing cytotoxic activity in nano grams level. Also result indicates a remarkably high selectivity index (6185.18) implying the potent cytotoxic effect against human rhabdomyosarcoma with lower cytotoxicity level for normal CC-1 epithelial cells. Thereby, inoscavin A can be developed as an effective anti-cancer drug for rhabdomyosarcoma. The novel isolation method accelerates the production of inoscavin A in good quality in order to use it effectively in the production of antitumor pharmaceutical compositions.

DETAILED DESCRIPTION OF THE INVENTION

Figure 1:
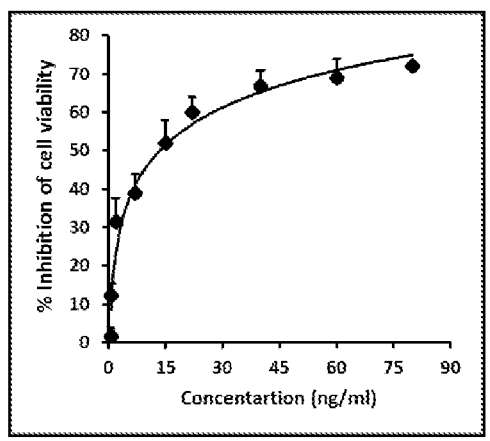
FIG. 1 depicts the percentage inhibition of cell proliferation against RD cell line as determined by MTT assay, after 24 hour treatment with the inoscavin A. The graphical data are represented as mean±SD of three independent experiments.

The present invention relates to a method belongs to the pharmaceutical field, in particular, a novel method to isolate known natural flavonoid, inoscavin A from fruiting bodies of *F. fastuosus* and its application as a novel drug lead for human rhabdomyosarcoma. The extraction is performed with an extraction solvent comprising one or more organic solvents and water. Examples of organic solvents that can be used according to the invention are methanol, ethyl acetate, hexane and dichloromethane. Prior to extraction with the polar organic solvent, the mushroom material may be ground, shredded, macerated, or otherwise treated to increase its overall surface area. Extraction of *F. fastuosus* with the polar organic solvent methanol can be accomplished using a sonication extraction wherein small pieces of *F. fastuosus* are placed inside a porous thimble and continuously extracted with methanol at room temperature for several hours to several days, or preferably, extraction can be started by simply placing small pieces of *F. fastuosus* into a conical flask containing methanol and allowing the resulting mixture to sonicate at the room temperature for several hours.

Following extraction, the methanol extract was concentrated (i.e., evaporated), in vacuo to obtain the dried methanol extract. Resulting dried extract was dissolved in water and partitioned in to non-polar organic solvent preferably, hexane by liquid-liquid extraction using a separatory funnel. Remainder in water was partitioned in to less polar/medium polar organic solvents preferably dichloromethane and ethyl acetate. Ethyl acetate fraction was dispensed from the separatory funnel and evaporated in a rotary evaporator to obtain the dried extract. Dried fraction is then purified to afford the present compound in purified form. The dried extract can be purified preferably via column chromatography and preparative HPLC. Preferably, the ethyl acetate extract is first purified using conventional silica gel chromatography to afford a series of fractions that are enriched with the present compound. Preferred fractions with the present compound were dried and preferably washed with acetone to remove any pigments or impurities as desired compound inoscavin A was not dissolved in 100% acetone. The purified yellow colour product; inoscavin A can be obtained using reverse phase preparative HPLC in pure form. After purification, the product can be dried using freeze-drying method. The structure of the isolated product was elucidated by means of combination of one and two-dimensional NMR experiments, including $^1$H-NMR (proton NMR), $^{13}$C-NMR, DEPT$^{13}$C-NMR (Distortionless Enhancement Polarization Transfer $^{13}$C NMR), H-H Correlation Spectroscopy (COSY), Heteronuclear Single Quantum Correlation (HSQC), Heteronuclear Multiple Bond Correlation (HMBC), Nuclear Overhauser Effect Spectroscopy (NOESY). In addition, HREIMS (High Resolution Electrospray Ionization Mass Spectrometry) was performed to obtain the high resolution mass spectrum.

Further, antiproliferative activity of isolated product inoscavin A against RD cells and CC-1 cells was determined using MTT assay. Results indicate that inoscavin A strongly inhibits the growth of human rhabdomyosarcoma (RD) cells, but not the growth of normal epithelial cells (CC-1) significantly (SI=6185.18). Apototic features observed by ethidium bromide/acridine orange staining of treated cells confirmed the apoptosis induced by inoscavin A. Therefore, this isolated compound is highly effective for RD cells and is suitable candidates for treatment of rhabdomyosarcoma. It can be developed as an antitumor pharmaceutical composition that can be admixtured with one or more pharmaceutically acceptable carriers. Further research on animal models and human beings will be important to administer the formulated product directly as a drug for RMS patients. For formulation of the compositions of the product, powder of the compound may be used in that form directly as a loose powder or encapsulated powder. Compositions may also include flavors, colorings and coatings. However, added agents must be non-toxic and should not strikingly interfere with the activity of the test compound. In addition, it can be added to fruit juice, vegetable juice or all kinds of nutrient drinks containing nutraceuticals of choice such as vitamins, minerals.

Materials and Methods (i) Collection of the Fungal Material and Preparation of the Extract The specimen of *F. fastuosus* was collected from the dry zone forest reserves in Sri Lanka during the period of September 2012 to October 2013. They were collected into paper bags and packed loosely with proper ventilation during the transportation. The identity of the specimen was achieved by the Department of Plant Sciences, Faculty of science, University of Colombo, Sri lanka (Genbank Accession No.: KP757737). Voucher specimens were deposited at the same institute (UOC:DAMIA:D26).

Mature fruiting bodies of *F. fastuosus* were brush cleaned, dried in the oven at 40° C. to a constant mass and pulverized. Shredded and ground mushroom material of fruiting bodies from *F. fastuosus* (1 kg) was added to a conical flask and allowed to extract by sonication in 4 L of methanol for 5-6 hours at room temperature. Methanol extract was filtered twice through whatman No. 1 filter and same extraction procedure was repeated for residue. Filtrates were combined and evaporated to dryness at 40° C. under reduced pressure using rotatory evaporator to completely dry the methanol. The resulting dried methanol extract was dissolved in minimum amount of water with maximum solubility and partitioned in to hexane by liquid-liquid extraction. Remainder in water was partitioned in to dichloromethane. Dichloromethane layer was dispensed and aqueous layer was extracted in to ethyl acetate using same extraction procedure. Ethyl acetate fraction was evaporated in a rotary evaporator to yield dried extract.

(ii) Isolation of Inoscavin a by Normal Phase Column Chromatography

The ethyl acetate extract was fractionated by normal phase column chromatography using the following protocol.

The dried ethyl acetate extract was dissolved in a minimum amount of methanol and added to 50 g of silica gel (230-400 mesh, 60 Å). The resulting silica gel slurry was then dried using rotary evaporation and placed at the top of 50 mm diameter column producing a final bed height of 200 mm. The column of silica was eluted, using a gradient solvent system starting from 1:1 ethyl acetate: hexane to 4:1 ethyl acetate: hexane (300 ml each in 5% step gradient), yielded fractions (25 ml each) number 20-23 was comprised the compound inoscavin A and evaporated the preferred fractions by air-drying. Dried fractions were further washed with acetone to remove any contaminations and spotted on silica gel plates to give a consolidated under 365 nm UV lamp. Further purifications were performed using reverse phase preparative HPLC to obtain the purified product of inoscavin A.

(iii) Purification by High Performance Liquid Chromatography (HPLC)

Dried compound was further purified by a recycling preparative-HPLC (Model LC-908, JAI Co., Japan) eluting with a linear gradient from 9:1 to 3:7 water: methanol acidified with 0.04% trifluoroacetic acid at a flow rate of 5 mL/min. Prime sphere $C_{18}$ HC (10 g) 50×250 mm with a 50×30 mm guard column was used in the preparative HPLC. In this manner, purified HPLC fraction comprising the compound inoscavin A was obtained and the product can be dried using freeze-drying methods in order to obtain the amorphous yellow colour powder of inoscavin A. All chromatographic runs were performed at ambient temperature using HPLC grade solvents.

(iv) Identification and Characterization of the Compound by Nuclear Magnetic Resonance (NMR) and Mass Spectrometry (HREIMS)

Nuclear magnetic resonance (NMR) spectra were recorded on a Bruker avance AV-400 or 500 MHz spectrometer in deuterated acetone:methanol (1:1) mixture. One and two-dimensional NMR experiments, including $^1$H-NMR, $^{13}$C-NMR, Distortionless Enhancement Polarization Transfer $^{13}$C NMR (DEPT$^{13}$C-NMR), H-H Correlation Spectroscopy (COSY), Heteronuclear Single Quantum Correlation (HSQC), Heteronuclear Multiple Bond Correlation (HMBC), Nuclear Overhauser Effect Spectroscopy (NOESY) provided molecular structure information. In addition, High Resolution Electrospray Ionization Mass Spectrometry (HREIMS) was performed to obtain the high resolution mass spectrum.

(v) Cell Lines and Cell Culture

RD and CC-1 cell lines were cultured in DMEM supplemented with 10% heat inactivated fetal bovine serum (FBS), 3% glutamine, sodium bicarbonate and antibiotic (penicillin/streptomycin). The cells were incubated at 37° C. in a humidified $CO_2$ incubator.

(vi) MTT Assay

Antiproliferative activities of inoscavin A against RD and CC-1 cells were determined using MTT (3, 4, 5-(dimethyl-thiazol-2-yl) 2-5-diphenyl tetrazolium bromide) assay. Metabolically active cells reduce MTT in to purple colored formazan crystals. Adherent cell lines were transferred with 0.12% trypsin and 0.5% EDTA and cells ($2 \times 10^5$ cells/well) were seeded in 24-well plates and incubated overnight with 1 mL of the DMEM medium described above. The stock solution of inoscavin A was prepared in DMSO at a concentration of 1 mg/ml and subsequently diluted up to 1000 ng/ml in order to prepare the working standards. The resulting monolayers of RD cells and CC-1 cells (70% confluence) were treated with different concentrations of the test solution and incubated for 24 hours at 37° C.

In all experiments, cycloheximide (5 mM, 50 µl) was used as the positive control and negative control contained 0.25% DMSO in growth media. The culture medium was replaced with fresh medium (1 ml) after 24 hours and MTT (5 mg/ml; 100 µl) was added to each well. The cells were incubated at 37° C. for 3 hours and the medium was aspirated carefully. The remaining formazan crystals were solubilized with 750 µl of 0.05 M HCl (in 2-propanol) and absorbance was measured at 570 nm. Percentage cell viability was determined using the equation below.

$$\text{Percentage cell viability} = \left[ \frac{\text{Absorbance of control} - \text{Absorbance of treated cells}}{\text{Absorbance of control}} \right]$$

The net absorbance from the wells of the untreated cells (negative control) was taken as the 100% viability. $IC_{50}$ of the test solution against RD cells was determined by regression analysis of the corresponding dose response curve. $CC_{50}$ of the test solution against CC-1 cell line was also calculated using the regression analysis. Safety of the compound for normal cells was determined in terms of selectivity index (SI) by calculating the ratio of $CC_{50}/IC_{50}$. SI value>2 is considered as safe.

The morphological changes of RD cells and CC-1 cells after the treatment with different concentrations of the test solution over 24 hours were detected by microscopic examination of cells. Morphological changes were compared with the negative and positive controls under fluorescence microscope.

(vii) Ethidium Bromide and Acridine Orange Staining

Ethidium bromide and acridine orange staining were performed to investigate the apoptosis induced by inoscavin A against RD cells. Ethidium bromide (EB) is only occupied by cells with damaged cell membranes. Acridine orange (AO) permeates via both live and dead cells. Cells were seeded in chamber slides and the confluent layer was treated with the test solution containing inoscavin A at different concentrations for 24 hours at 37° C. as described previously. The adherent cells were washed with 200 µL of PBS and 2 µL of the dye mixture containing ethidium bromide (100 mg/mL) and acridine orange (100 mg/mL) was placed on each well of the chamber slide. Chamber slides were examined immediately under the fluorescence microscope. Images were photographed using a Nikon D 700 camera connected to the microscope.

Result (i) Structure Elucidation of the Flavonoid Compound Inoscavin a of Formula 1

The chemical structure of the isolated compound was determined by spectroscopic methods including 1D and 2D NMR experiments. Inoscavin A compound was obtained from reverse phase preparative HPLC, as a yellow colour amorphous solid, and identified as 2-(3,4-dihydroxyphenyl)-6-[(E)-2-(3,4-dihydroxyphenyl)ethenyl]-5'-methylspiro[2H-furo[3,2-c]pyran-3,2'-furan]-3',4-dione. Its molecular formula, $C_{25}H_{18}O_9$, was determined by HREIMS (High resolution electrospray ionization mass spectrometry) m/z 462 g/mol and by means of combination of the $^1$H-NMR, $^{13}$C-NMR, DEPT$^{13}$C-NMR, COSY, HMQC, HMBC and NOESY. Table 1 lists the assigned $^{13}$C and $^1$H chemical shifts for the present compound. The spectral data were in good agreement with those of inoscavin A, which was previously reported from the methanolic extract of *Inonotus xeranticus* by Kim J, Yun B, Shim Y K, Yoo I (1999).

Inoscavin A, A New Free Radical Scavenger from the Mushroom *Inonotus xeranticus*. Tetrahedron Letters. 40: 6643-66.

TABLE-1

$^{13}$C- and $^{1}$H-NMR chemical shift values of compound 1
(ppm, MeOD + C3D6O, 125 and 400 MHz respectively)

| C. No. | $\delta_C$ | $\delta_H$ (J, Hz) |
|---|---|---|
| 1 | 160.3 | — |
| 2 | 99.7 | — |
| 3 | 176.6 | — |
| 4 | 95.8 | 6.51 |
| 5 | 166.9 | — |
| 6 | 116.8 | 6.75 d (15.6) |
| 7 | 139.7 | 7.43 d (15.6) |
| 8 | 128.5 | — |
| 9 | 115.1 | 7.08 br s |
| 10 | 149.4 | — |
| 11 | 147.8 | — |
| 12 | 116.6 | 6.79 d (8.4) |
| 13 | 122.6 | 7.01 br d (8.4) |
| 1' | 192.6 | — |
| 2' | 105.1 | 5.57 s |
| 3' | 202.8 | — |
| 4' | 95.5 | — |
| 5' | 95.6 | 5.65 s |
| 6' | 123.2 | — |
| 7' | 115.9 | 6.76 br s |
| 8' | 146.9 | — |
| 9' | 146.3 | — |
| 10' | 115.5 | 6.72 d (8.4) |
| 11' | 120.3 | 6.59 br d (8.4) |

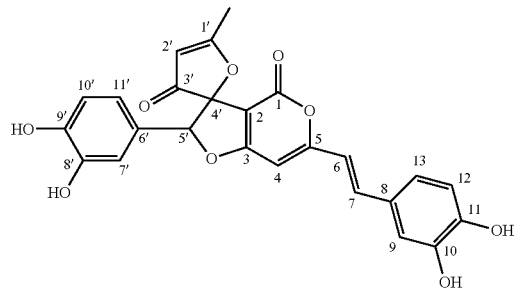

Formula 1

(ii) Cytotoxicity Effect of Compound Inoscavin A of Formula 1

The purified compound inoscavin A exhibited a promising cytotoxic effect against RD cells in a dose-dependent manner. As evident in FIG. 1, dose dependent increase for in vitro cytotoxicity was observed over a range of 2-60 ng/mL of test solution against RD cell line. Interestingly, a maximum of 75% inhibition of cell growth was observed at concentrations over 60 ng/mL to 100 ng/mL. Interestingly, the $IC_{50}$ value obtained for the mean of the three independent sample preparations against RD cells was 27.99 nM. Positive control (cycloheximide) exhibited 78.45±2.22% growth inhibition at the concentration (5 mM, 50 µL) used. The $IC_{50}$ value obtained for the mean of the three independent sample preparations against normal mammalian cell line (CC-1) was 167 µM. Thereby, selectivity index shown by the compound inoscavin A was a remarkably high value (6185.18) conveying that product inoscavin A is capable to provide a significant protection for normal cells compared to the tumor cells.

Figure 2:
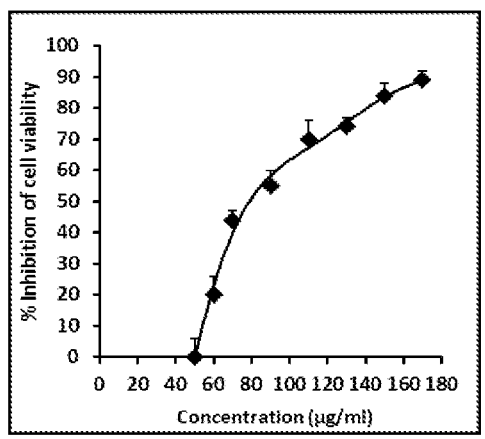
FIG. 2 demonstrates the percentage inhibition of cell viability against CC-1 cell line as determined by MTT assay, after 24 hour treatment with the inoscavin A. The graphical data are represented as mean±SD of three independent experiments.
Figure 3:
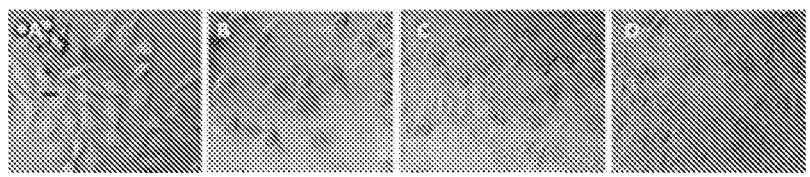
FIG. 3 depicts light micrographs of RD cell line after 24 hours of incubation with the inoscavin A at different concentrations. A—negative control; B—cycloheximide as the positive control (5 mM; 50 μL); C—15 ng/mL; D—50 ng/mL. Live cells have characteristic polygonal shape and dead cell are rounded. Reduction in cell density was also observed in positive control and the treated cells with highest concentration (original magnification 20×).
Figure 4:
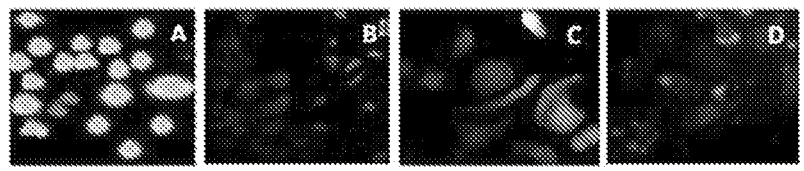
FIG. 4 shows apoptotic morphology detection by acridine orange-ethidium bromide (AO/EB) fluorescent staining of RD cell line treated with the inoscavin A. A—negative control; B—cycloheximide as the positive control (5 mM; 50 μL); C—15 ng/mL, D—50 ng/mL of the test solution. Nuclei stained with green colour indicate live cells while greenish yellow shows early apoptotic cells. Orange red nuclei demonstrate late apoptotic cells whereas red colour indicates dead cells (some cells are fragmented and become faded). This figure denotes the results of at least 3 independent experiments (original magnification 40×).
Figure 5:
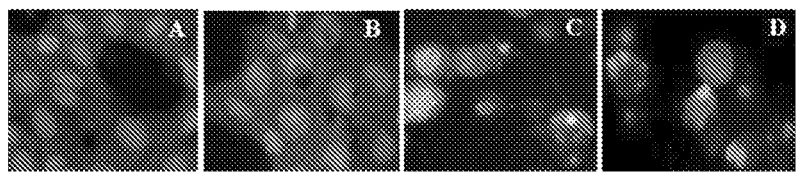
FIG. 5 demonstrates the characteristic morphology of live CC-1 cells at low concentrations below 50 μg/ml and apoptotic morphology of concentrations above 50 μg/ml. A—negative control; B—45 μg/mL; C—120 μg/mL; D—150 μg/mL (original magnification 40×).

The morphological changes observed on RD cells after treatment of test solution are represented in FIG. 2. The cell morphology of untreated cells appeared in elongated shape and treated cells appeared with cellular shrinkage, oval or irregular in shape and condensed cytoplasm. The cells treated with highest concentration of the inoscavin A (50 ng/mL) displayed the detached and round shape dead cells as indicated in FIG. 2.

(iii) Ethidium Bromide/Acridine Orange Staining

Cell morphology of treated cells was further analyzed by ethidium bromide/acridine orange staining. Morphological changes of untreated cells (negative control) appeared with the normal nuclei presented in bright green. Apoptotic cells will be stained in orange or red with acridine orange depending on the degree of loss of membrane integrity and co-staining with ethidium bromide. Cells stained with AO/EB in yellowish green indicate the signs of early apoptosis and orange red represents late apoptotic cells. Dead cells appeared in red. Unique features of apoptotic cells such as chromatin condensation, nuclear fragmentation, presence of apoptotic bodies and blebbing formation were also evident upon examination of stained cells with ethidium bromide/acridine orange. Chromatin condensation and nuclear fragmentation were predominantly observed apoptotic features for treated cells with high concentrations of the extract. Moreover, number of apoptotic cells was gradually increased with the treatment dose.

Discussion

Extraction method for isolation of a natural product is primarily based on the separation of analytes from the cellular matrix of the natural source. Predominantly, desorption of the solutes from the active sites of the matrix and diffusion into the matrix itself, solubilization of the analyte in the extractant, diffusion of the compound in the extractant and collection of the extracted solutes are the major concerns in the process of extraction and recovery of a solute from the cellular matrix of biogenic material. Preferably, an extraction process should be rapid, simple, inexpensive and comprehensive with respect to the constituents to be isolated. The increasing interest in plant and mushroom metabolites makes it necessary to expand the current extraction protocols. In current invention, a simple, highly demanding and rapid method has been described to isolate inoscavin A from *F. fastuosus* compared to other reported isolation methods to extract inoscavin A from *Phellinus* species. Isolation of the product of inoscavin A mainly combines two separation techniques, reverse phase preparative high-performance liquid chromatography (HPLC) and normal phase column chromatography with a large bed size (50×200 mm). Components of the extract are better separated with a larger bed size. Therefore, larger bed size has been chosen for the separation. The choice of different separation steps is of great importance and an analytical-scale optimization of the separation parameters is worthwhile. All separation procedures involve the division of a mixture into a number of discrete fractions. These fractions may be physically separate divisions, such as the two phases of a liquid-liquid extraction, or they may be the contiguous eluate from a chromatography column. Usually, a column is run and the eluate divided to a manageable number of even-sized fractions. In current invention, fractions number 20-23 which are obtained from the normal phase column chromatography were concentrated using air-drying method and spotted on silica gel plates to give a consolidated under 365 nm UV lamp; displayed a strong yellow colour fluorescence. Dried fractions were further purified by washing with acetone to dissolve any pigments or impurities in acetone as compound inoscavin A was not dissolved in 100% acetone. Inoscavin A, a yellow colour amorphous powder can be obtained in substantially purified form (≥98%) using recycling reverse phase preparative HPLC. HPLC is a highly demanding liquid chromatographic technique which is used to separate the components in a mixture. The purified product can be dried using freeze-drying method and structure of the compound was elucidated precisely by means of combination of $^1$H-NMR, $^{13}$C-NMR, DEPT $^{13}$C-NMR, 2D NMR (COSY, HSQC, HMBC, NOESY) and ESI-MS techniques. Specifically, NMR spectroscopy provides detailed information regarding the structure, dynamics, reaction state and chemical environment of molecules.

The isolated product was investigated for anticancer properties against RMS using RD cell line. RD has been demonstrated to have amplification of the MYC oncogene, homozygous mutation of TP53 and Q61H mutation of NRAS. Cytogenetic analysis and DNA fingerprinting has been shown that medulloblastoma cell line (TE671) is likely to be a subclone of RD cells. Treatment of this cancer comprises of a combination of chemotherapy and radiation along with surgery. Dactinomycin, vincristine and ifosfamide, are most commonly preferred cancer drugs approved by the Food and Drug Administration (FDA) for rhabdomyosarcoma. dactinomycin, vincristine are infused intravenously by a dose of 1.5 mg/m2 (max 2 mg) for one day and ifosfamide is administered by a dose of 3 g/m2 for two days as therapeutic regimens. However, dactinomycin is also associated with high emetic potential similar to all synthetic anticancer drugs available; patients should receive antiemetics as prophylaxis and is highly corrosive to soft tissue leading to tissue damage if extravasation occurs. Also it causes alopecia in most patients. In addition, vincristine Sulfate is commonly associated with neurotoxicity, including sensory and motor neuropathies, which is typically dose-related. Neurotoxicity is generally reversible, though recovery may be gradual and may not be complete. Vincristine also causes constipation which can be severe. Consequently, they produce unpleasant side effects which are commonly associated with chemotherapy including anemia, hair loss, urination changes, bleeding problems, nausea and vomiting. In addition, modern chemotherapeutic agents for treating RD have been found to have several toxic effects such as hepatotoxicity and cardiotoxicity. Hence, use of this natural product in tested against RD is an extremely promising strategy for cancer prevention today.

In current invention, we showed that inoscavin A product isolated from *Fulviformes fastuosus* has miraculous anticancer properties ($IC_{50}$=27.99 nM) with remarkably less cytotoxicity effect on normal epithelial cells (SI=6185.18). Cytotoxic activity was determined by MTT cell viability assay which is a well-established colorimetric method to assess the cell proliferation and cell viability. MTT induced cell death in RD cells of mangiferin which is isolated from plant *Mangifera indica* has shown an inhibitory concentration ($IC_{50}$) of 70 µM. Interestingly, antiproliferative activity of inoscavin A was found to be approximately 2500 times greater than the activity shown by mangiferin. Above innovation implies the propensity of inoscavin A to develop as a safe pharmaceutical composition against RMS with high efficacy of inducing cell death of RD being less toxicity to normal cells. Morphological characterization via ethidium bromide and acridine orange staining indicates apoptotic features of treated cells as described above. It revealed that the mode of action of cell death induced by inoscavin A was mediated through apoptosis. It strengthens the results obtained by MTT assay. Importantly, inoscavin A possesses potent antiproliferative activity revealing its ethnopharmacological potential.

Intriguingly, present invention provides a method which is convenient and high in extraction efficiency to isolate inoscavin A as a stable and quality product. This novel method can be effectively used for the preparation of antitumor drug using inoscavin A. It can be formulated in to tablets, capsules, caplets or similar dosage forms. Initially, formulated product should be tested by carrying out animal studies followed by human clinical trials. Fascinatingly, most of the mushrooms belong to the family hymenochaetaceae of *F. fastuosus* have been used as edible forms. Therefore, inoscavin A has a greater potential to act safely in human body without creating any complications. Also, this fact was supported by the remarkably high selectivity index shown by the inoscavin A which implies the less toxicity for normal mammalian cells. The product may be administered alone or as an active ingredient in pharmaceutical compositions including non-toxic, pharmaceutically acceptable carriers. The dosage of the product to be administered depends upon many factors such as the particular form of the compound; the stage of the disease; the age, weight and clinical condition of the patient; any concurrent therapeutic treatments; and the experience and judgment of the clinician for administering the therapy. The composition may be administered orally, intravenously at a dosage range and frequency or intraperitoneally.

Currently, several companies are dedicated to prepare anti-cancer formulae from mushroom extracts using state-of-the-art technology and their products are gradually being recognized globally. Zhejiang Fangge Pharmaceutical & Healthcare Products Co. Ltd., a huge pharmaceutical company in China specializes in development and marketing of mushroom products for anti-cancer uses. Unambiguously, present invention is set to create a revolution in therapeutic strategies in curbing rhabdomyosarcoma. In addition, present invention provides a scientific proof of the traditional awareness in using natural compounds isolated from medicinal mushrooms as an anticancer agent.

REFERENCED BY

| Citing Patent | Filing date | Publication date | Applicant | Title |
|---|---|---|---|---|
| CN102977114B | 20 Nov. 2012 | 14 Jan. 2015 | 浙江省中医药研究院 | Inoscavin A as a monomeric component in *phellinus* as well as prepearation method and application thereof |

-continued

| Citing Patent | Filing date | Publication date | Applicant | Title |
|---|---|---|---|---|
| CN103864738A | 17 Jan. 2014 | 18 Jun. 2014 | 六安市丹皇生物科技有限责任公司 | *Phellinus* monomer component *Phellinus igniarius* E and inoscavin A and preparation method thereof as well as application of *Phellinus igniarius* E and inoscavin A in anticancer drugs |

The invention claimed is:

1. A method to isolate inoscavin A comprising:
    (a) providing Fulviformes fastuosus fruiting bodies;
    (b) pulverization and sonication extraction of the Fulviformes fastuosus fruiting bodies to obtain an extract;
    (c) partitioning of the extract of step (b) using liquid-liquid extraction;
    (d) fractionation of extract from step (c) using column chromatography; and
    (e) purification of product from step (d) using high performance liquid chromatography.

2. The pulverization and sonication in claim 1 wherein, the Fulviformes fastuous fruiting bodies is pulverized into a fine powder.

3. The pulverization and sonication in claim 1, step (b), wherein the extraction is performed into a polar organic solvent comprising methanol and obtaining a dried extract.

4. The liquid-liquid extraction in claim 3 comprising dissolving the dried extract in water and transferring the dissolved extract into a separatory funnel containing hexane and obtaining an aqueous layer containing the extract.

5. The liquid aqueous layer of claim 4 wherein the aqueous layer containing the extract was further extracted using ethyl acetate and dried.

\* \* \* \* \*